(12) United States Patent
Madsen et al.

(10) Patent No.: US 7,293,561 B2
(45) Date of Patent: Nov. 13, 2007

(54) LOW PROFILE ADAPTER FOR TRACHEAL TUBES

(75) Inventors: Edward B. Madsen, Riverton, UT (US); Scott M. Teixeira, Draper, UT (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 0 days.

(21) Appl. No.: 11/211,266

(22) Filed: Aug. 25, 2005

(65) Prior Publication Data

US 2007/0044806 A1 Mar. 1, 2007

(51) Int. Cl.
*A61M 16/00* (2006.01)
*A62B 9/06* (2006.01)

(52) U.S. Cl. .......................... 128/207.14; 128/207.15; 128/207.16; 128/200.26; 604/96.01; 604/101.03

(58) Field of Classification Search ........... 128/207.14, 128/207.15, 207.16, 200.26; 604/96.01, 604/101.03, 118, 268, 316
See application file for complete search history.

(56) References Cited

U.S. PATENT DOCUMENTS

| | | | |
|---|---|---|---|
| 2,791,217 A | 5/1957 | Iskander | |
| 4,305,392 A | 12/1981 | Chester | |
| 4,327,721 A | 5/1982 | Goldin et al. | |
| 4,469,090 A | 9/1984 | Konomura | |
| 4,607,635 A | 8/1986 | Heyden | |
| 4,840,173 A | 6/1989 | Porter, III | |
| 4,881,542 A | 11/1989 | Schmidt et al. | |
| 5,067,497 A | 11/1991 | Greear et al. | |
| 5,140,983 A | 8/1992 | Jinotti | |
| 5,143,062 A * | 9/1992 | Peckham | 128/207.14 |
| 5,311,864 A * | 5/1994 | Huerta | 128/207.15 |
| 5,360,413 A | 11/1994 | Leason et al. | |
| 5,372,131 A * | 12/1994 | Heinen, Jr. | 128/207.15 |
| 5,490,503 A | 2/1996 | Hollister | |
| 5,582,167 A | 12/1996 | Joseph | |
| 5,687,714 A | 11/1997 | Kolobow et al. | |
| 5,803,078 A | 9/1998 | Brauner | |
| 5,819,723 A | 10/1998 | Joseph | |
| 5,819,733 A * | 10/1998 | Bertram | 128/207.15 |
| 5,832,920 A * | 11/1998 | Field | 128/207.14 |
| 5,845,634 A * | 12/1998 | Parker | 128/200.26 |
| D412,984 S * | 8/1999 | Cover et al. | D24/129 |
| 6,062,223 A * | 5/2000 | Palazzo et al. | 128/207.15 |
| 6,460,540 B1 * | 10/2002 | Klepper | 128/207.14 |
| 2005/0182291 A1 | 8/2005 | Hirata | |
| 2006/0207602 A1* | 9/2006 | Kolobow et al. | 128/207.14 |

(Continued)

FOREIGN PATENT DOCUMENTS

DE 2939794 4/1981

(Continued)

*Primary Examiner*—Patricia Bianco
*Assistant Examiner*—Nihir Patel
(74) *Attorney, Agent, or Firm*—James B. Robinson; Scott Garrison

(57) ABSTRACT

An adapter for use on a suction lumen of a catheter is disclosed. The adapter is capable of extending the suction capabilities of the catheter to a point distal to a suction port in the catheter. The adapter is at least partially inserted into the catheter. The adapter contains a plug and a duct. The duct has an inlet and an outlet. The duct effectively extends the reach of a suction source and the plug is adapted to seal the catheter between the adapter and the distal end.

10 Claims, 6 Drawing Sheets

U.S. PATENT DOCUMENTS

| | | | |
|---|---|---|---|
| 6,550,475 B1 * | 4/2003 | Oldfield | 128/200.26 |
| 6,796,309 B2 * | 9/2004 | Nash et al. | 128/207.14 |
| 7,089,942 B1 * | 8/2006 | Grey | 128/207.14 |
| 2002/0014238 A1 | 2/2002 | Kotmel | |
| 2004/0011364 A1 | 1/2004 | Dhuper et al. | |
| 2004/0255951 A1 | 12/2004 | Grey | |

FOREIGN PATENT DOCUMENTS

| | | |
|---|---|---|
| EP | 0766976 A2 | 4/1997 |
| GB | 2199630 | 7/1988 |
| GB | 2207736 | 2/1989 |
| JP | 2005177134 | 7/2005 |
| WO | WO93/09833 | 5/1993 |
| WO | WO99/38548 | 8/1999 |
| WO | WO 2005/009522 | 2/2005 |

* cited by examiner

LOW PROFILE ADAPTER FOR TRACHEAL TUBES

BACKGROUND

The present invention relates to medico-surgical tubes and assemblies. The invention is more particularly concerned with cuffed medico-surgical tubes, such as, for example, cuffed tracheal tubes in which an inflatable cuff seals the tube with a patient's trachea.

For example, the conventional method of endotracheal intubation involves the insertion of a tubular device (an endotracheal tube) into the trachea. The endotracheal tube continues through the trachea and stops above the carina anterior to a position between the 2nd and 4th thoracic vertebrate, allowing the gases to be directed through the tube and into the lungs.

A primary objective of the treatment is the mechanical ventilation of the patient's lungs. This function normally induced by the patient's breathing, is typically impaired by the disease or injury being treated. In order to create the air pressure necessary to artificially ventilate the lungs, the passageway around the tube must be sealed. This is accomplished by a balloon or inflatable cuff provided around the tube. With the tube in place, the cuff is located about 3 to 5 centimeters above the carina and within the tube-like trachea.

The cuff is inflated to expand against the wall of the trachea and thereby to prevent gases that are being pumped into the lungs from simply backing up and escaping around the tube. This method of treatment has been quite successful for patients with chronic and acute respiratory disease. However, the method is not without complications.

Many intubated patients receiving the artificially induced ventilation may develop pneumonia. This pneumonia, known as Ventilator-Associated Pneumonia or VAP results from an infection of the lungs when pooled secretions, which have become infectious, are allowed, as a result of by-passing the upper airway, to enter the lungs. Unfortunately, this has been almost impossible to avoid with the prior endotracheal tubes.

The epiglottis is a form of valve that normally functions to selectively close the entry to the trachea and protect the airways (trachea and lungs) from secretions and particulate matter. The insertion of the endotracheal tube by-passes the protective system of the tracheo bronchial tree. Secretions that would normally be directed harmlessly through the digestive system follow the path of the tube, into the airway. The cuff above the carina blocks the downward flow of these secretions thus preventing them from entering the lungs. The secretions become pooled above the cuff and if unattended, rapidly grow infectious bacteria that pose a serious risk to the patient.

The problem of these prior endotracheal tubes arises primarily upon cessation of the mechanical ventilation. The cuff is deflated in order to withdraw the endotracheal tube from the trachea. The infected fluid is now released to continue passage down the trachea and into the highly susceptible lungs where bronchitis or pneumonia develops rapidly. Whereas deflation of the cuff in the presence of the pooled secretions poses the greatest threat of lung infection, there is substantial risk also during treatment, i.e. with the cuff inflated. An incomplete seal caused by folds or creases in the cuff is not unusual and fluids can and do migrate along them into the lungs. Though the se folds or creases are not typically a problem to the ventilation treatment, because they do allow microaspiration of the pooled secretions past the cuff it is desirable to remove the secretions and not allow them to accumulate for very long.

Various proposals have been made previously for removing such secretions by providing a suction aperture above the cuff. In Heyden U.S. Pat. No. 4,607,635 there is described a tracheal tube having a channel which opens at various locations along its length and through which a suction catheter can be inserted to remove secretions at any desired location above the cuff. In Chester U.S. Pat. No. 4,305,392 there is described a tracheal tube with a bulbous chamber above the cuff in which secretions are collected for removal through a suction lumen extending through the wall of the tube. The problem with both of these tubes is that it is not possible to remove secretions that collect immediately above the cuff. This is because the cuff is conventionally attached to the wall of the tube by means of short collars at opposite ends of the cuff, which are adhered to the tube and extend above and below the cuff. The length of the collar above the cuff defines the closest distance by which the suction aperture can be spaced from the cuff, because any attempt to form a suction aperture through the collar would weaken the joint between the cuff and the tube which might possibly lead to leakage from the cuff. In Porter U.S. Pat. No. 4,840,173 there is suggested a way in which secretions close to the cuff could be removed, by providing a suction tube which projects over the proximal collar of the cuff. This, however, would have the disadvantage of being relatively complex and expensive to make and may provide an undesirable projection from the side of the tube which could irritate the delicate surface of the trachea. There is also the risk that the end of the suction tube may damage the cuff or become blocked by the cuff. This risk can be reduced by making the upper end of the cuff more rigid, but this is a further complication in the construction of the tube.

What is needed is a means for removing secretions that collect immediately above the cuff that is simple, works with any cuff and does not negatively impact the trachea or the integrity of the cuff.

SUMMARY OF THE INVENTION

The present invention improves upon an apparatus for removing secretions by providing a tracheal tube with a suction lumen and an adapter to extend the suction capabilities to a point distal to a suction port into the catheter. The apparatus in one embodiment is a cannula having a length defined by a proximal end and a distal end. The cannula has a respiratory lumen extending along the length and at least one suction lumen extending along the length. The suction lumen is disposed adjacent to an exterior wall of the cannula. A suction source is connected to the proximal end. The adapter is at least partially inserted into the exterior wall of the cannula at a position along the length of the cannula. The adapter contains a plug and a duct. The duct has an inlet and an outlet. The outlet interconnects the duct with the suction source through the suction lumen, whereas the inlet extends the reach of the suction lumen through the duct. The plug is adapted to seal the suction lumen between the adapter itself and the distal end. An inflatable cuff may be provided on the cannula. The inflatable cuff would be shaped to block the trachea beneath a glottis of the patient. The inlet of the adapter would be oriented such that suction occurs proximal to the inflatable cuff and may be made to overlap the collar portion of the cuff itself.

In certain embodiments, the adapter is permanently affixed to the exterior wall of the cannula. A piercing member may be provided. The piercing member is for piercing the exterior wall of the cannula thereby connecting the duct with the suction lumen. A plurality of barbs may be provided on the adapter and/or plug portion of the adapter to engage walls internal to the cannula.

In many embodiments, the adapter may be configured into the shape of a partial annulus or a ring. The adapter may be made of a flexible or inflexible material. Moreover, a plurality of inlets may be provided for accessing the duct.

Additional features may include providing the adapter with a first wall for seating against the exterior wall of the cannula and a second wall disposed a spaced distance from the first wall. The spaced distance would be the duct.

In another embodiment, the invention may simply be an adapter for insertion into a catheter. Such an adapter may have a first surface for seating upon an exterior wall of the catheter, a flange for contacting the exterior wall, a plug for engaging a lumen within the catheter, and a duct extending through the adapter. The duct would have an inlet spaced a distance from an outlet. The outlet would be adapted to communicate with the lumen through the insertion point, and the inlet would be adapted to effectively extend the reach of the lumen to a region external to the lumen. The plug would also serve to seal the lumen in one direction from an insertion point of the adapter into the catheter. As such, it may have a surface disposed opposite the flange. The plug working in conjunction with the surface of the flange would capture the exterior wall of the catheter and secure the adapter to the catheter.

Other objects, advantages and applications of the present invention will be made clear by the following detailed description of a preferred embodiment of the invention and the accompanying drawings wherein reference numerals refer to like or equivalent structures.

DETAILED DESCRIPTION

Reference will now be made to the drawings in which the various elements of the present invention will be given numeral designations and in which the invention will be discussed so as to enable one skilled in the art to make and use the invention. It is to be understood that the following description is only exemplary of the principles of the present invention, and should not be viewed as narrowing the pending claims. Those skilled in the art will appreciate that aspects of the various embodiments discussed may be interchanged and modified without departing from the scope and spirit of the invention.

Figure 1:
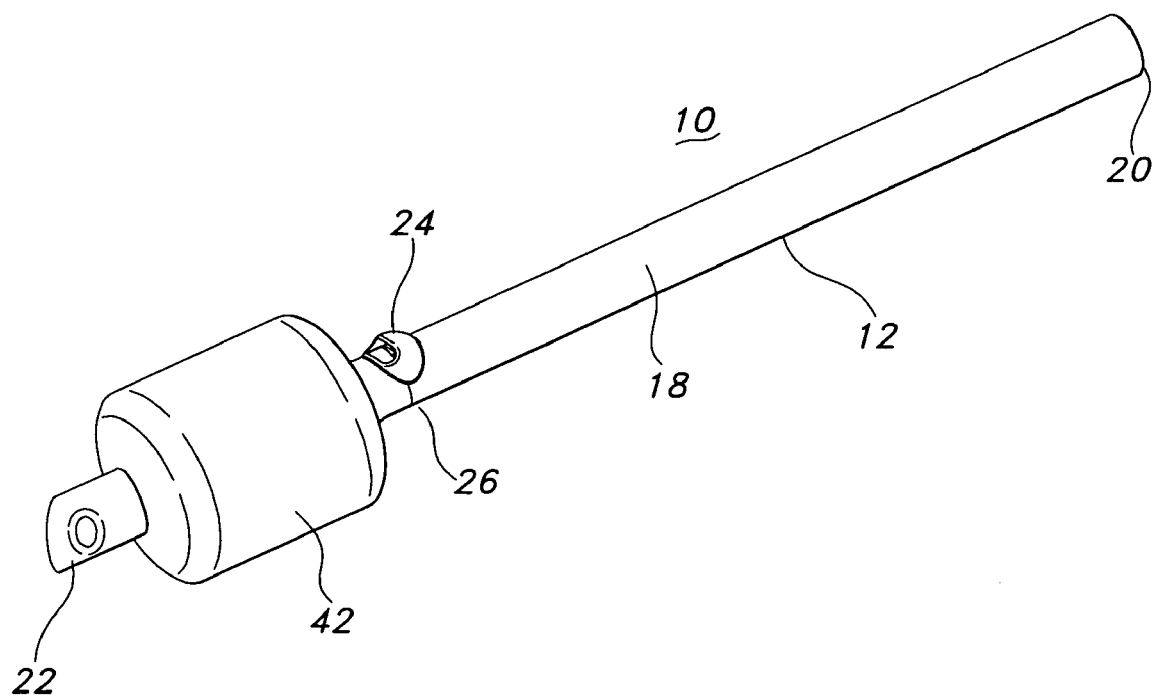
FIG. 1 is a front orthogonal view of one embodiment of a low profile adapter in use on a catheter in accordance with the present invention.
Figure 1A:
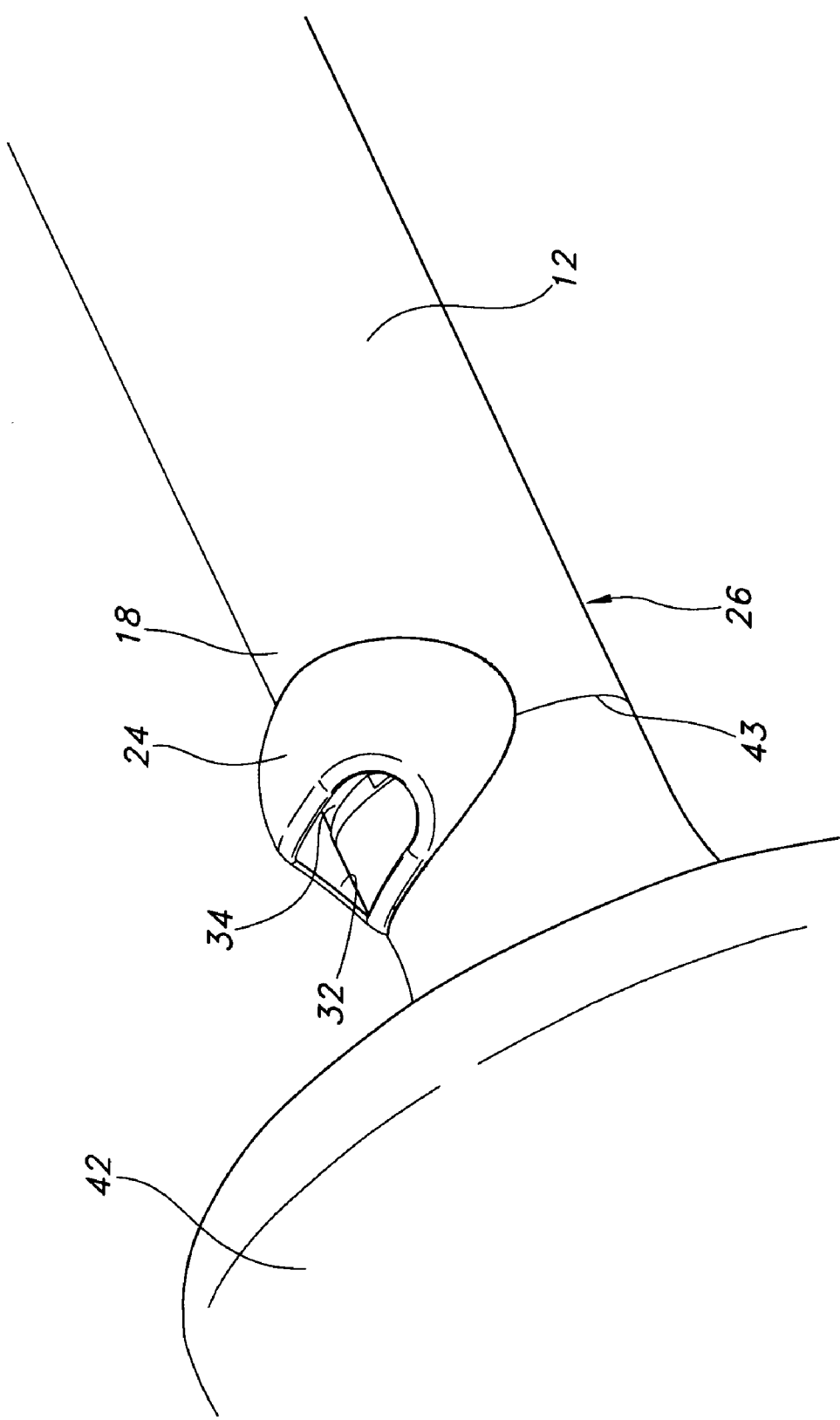
FIG. 1A is a magnification of the adapter portion of the FIG. 1 view.

Referring to FIGS. 1 and 1a, a tracheal tube 10 in accordance with one embodiment of the present invention is depicted. The tracheal tube 10 in the depicted embodiment is a multilumen cannula 12 having a length defined by a proximal end 20 and a distal end 22. An adapter 24 is partially inserted into an exterior wall 18 of the cannula 12 at a position 26 along the length. The tracheal tube 10 has an inflatable cuff 42 which is shaped to seat against and block a patient's trachea beneath the glottis. The cuff 42 is attached to the tube in a conventional manner at cuff collars 43.

Figure 2:
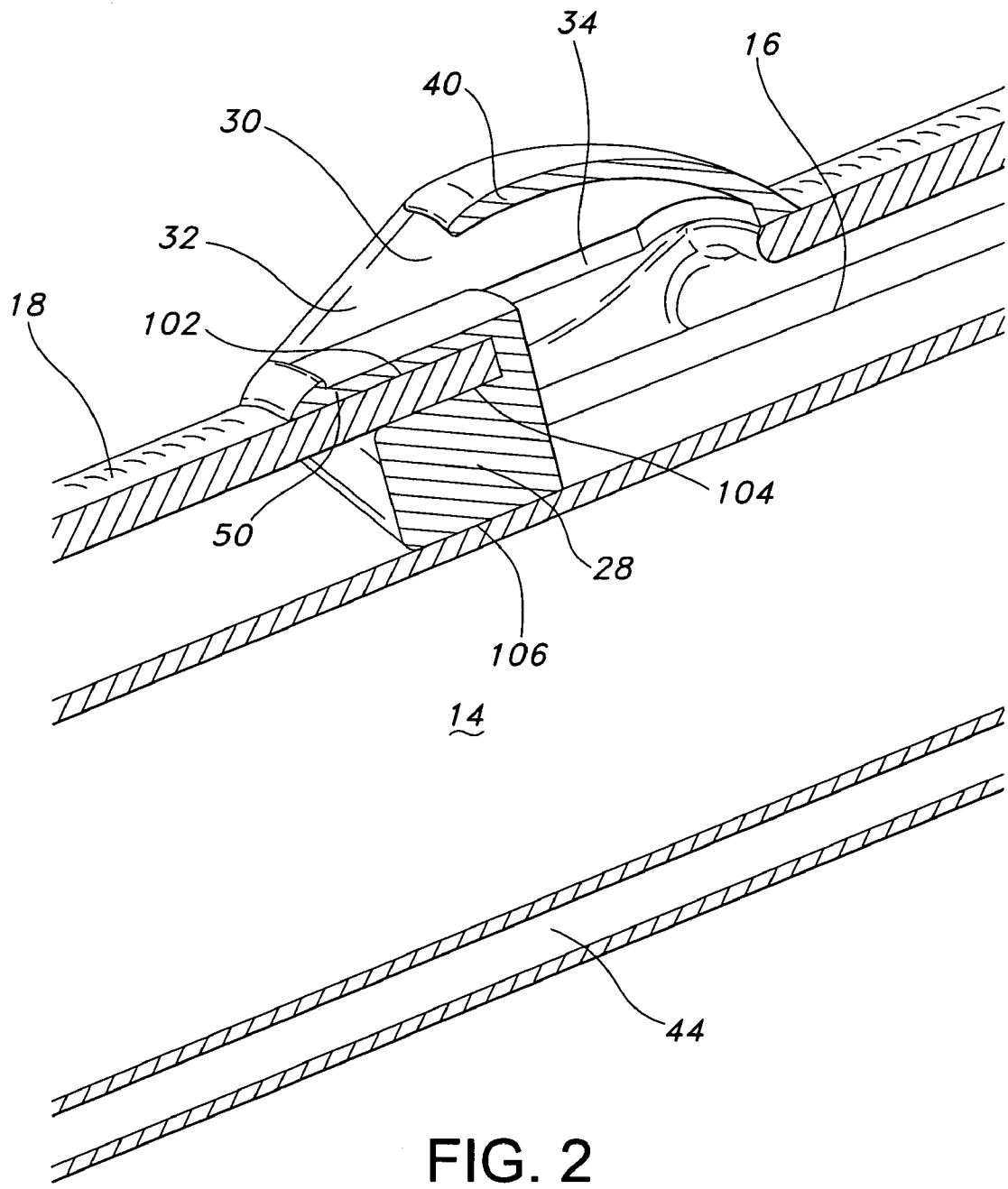
FIG. 2 is a sectional view of the adapter portion of FIG. 1 shown in relation to the lumens within the catheter.

Referring now to the FIG. 2 cross-sectional view, it can be seen that the cannula 12 contains at least one respiratory lumen 14 and at least one suction lumen 16 disposed adjacent to an exterior wall 18 of the cannula 12. The respiratory lumen 14 and the suction lumen 16 extend along the length of the cannula 12. A suction source (not shown) is connected to the proximal end 20 and used to create a vacuum or suction within the suction lumen 16. In this view, an inflation lumen 44 for inflating and deflating the cuff 42 is also shown.

Looking now to the adapter 24 on FIG. 2, it may be seen that it consists of two major portions, a plug 28 and a duct 30. The plug 28 is adapted to seal the suction lumen 16 between the position 26 of the adapter 24 and the distal end 22, as seen on FIGS. 1 and 1a. The plug 28 may also assist in securing the adapter 24 to the cannula 12. As may be seen a flange 50 in conjunction with the plug 28 serves to capture the exterior wall 18 of the cannula 12 between surfaces 102 and 104. Moreover surface 106 of the plug 28 seats against an interior wall 38 assisting this result. Barbs, prongs, or ridges may be provided upon any of these surfaces in order to better seat the adapter with the cannula 12.

Additionally or alternatively, the adapter 24 may also be permanently affixed to the exterior wall 18 of the cannula 12 at surface 102 by solvent bonding, ultrasonic welding, adhesive, or other suitable methods intended to permanently affix the components to one another. Depending upon the needs of the apparatus, the adapter 24 may be flexible or rigid and may be made of a biocompatible polymer. For example, flexible materials could be various blends of PVC, Polyurethane, or Silicone whereas rigid materials could be various blends of Polycarbonate, ABS, Polyether Imide or a higher durometer PVC than the flexible PVC.

Still looking at FIG. 2, it may be seen that the duct 30 of the adapter 24 has an inlet 32 and an outlet 34. The outlet 34 interconnects the duct 30 with the suction source through the suction lumen 16. The inlet 32 effectively extends the reach of the suction lumen 16 through the duct 30 a distance from the cannula exterior wall 18. As may be seen in FIGS. 1 and 1a, the inlet 32 may be oriented such that suction is directed toward a region proximal to the inflatable cuff 42. In this instance, the overall design intent is to overlap the cuff collar 43 thereby extending the suction closer to the cuff 42 while keeping the adapter inlet 32 close to the tube thereby minimizing trauma to the trachea and vocal cord during intubation.

Figure 3:
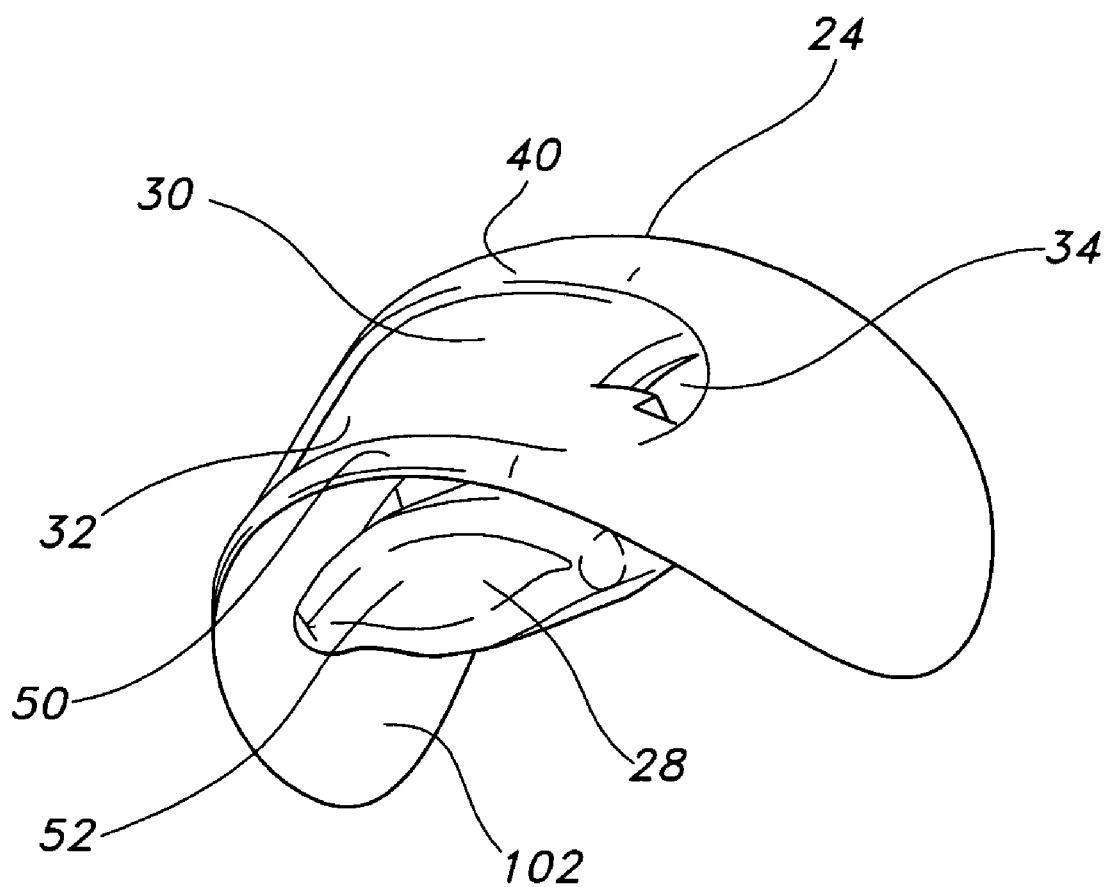
FIG. 3 is a front orthogonal view of the FIG. 1 low profile adapter.
Figure 4:
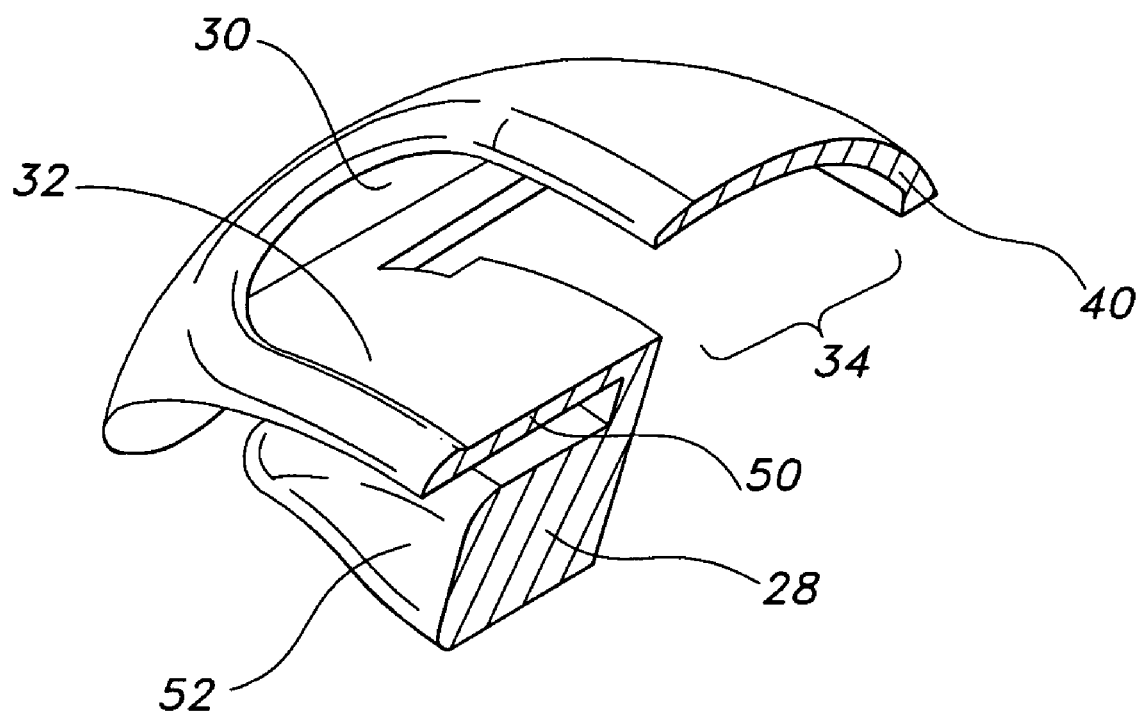
FIG. 4 is a sectional view of the FIG. 1 low profile adapter.

Looking at the adapter embodiment depicted in FIG. 3 and the cross-sectional view depicted in FIG. 4, it is evident that the adapter 24 may be configured as a partial annulus or partial ring. In this embodiment, the adapter 24 has an exterior wall 40 disposed a spaced distance from the flange 50. The spaced distance forms the volume of the duct 30. Due to the curvature and shape of the adapter 24, the volume of the duct 30 may be maximized maintaining a cross sectional area greater than or equal to the suction lumen 16 while also maintaining a low profile. For example, in one embodiment, the exterior wall 40 of the adapter 24 is envisioned to extend outward from the exterior wall 18 from about 0.5 mm to about 4.0 mm, for example in one embodiment it is envisioned that the adapter will extend about 2.5 mm from the exterior wall 18 of the adapter 24 and should not negatively affect the trachea.

Figure 5:
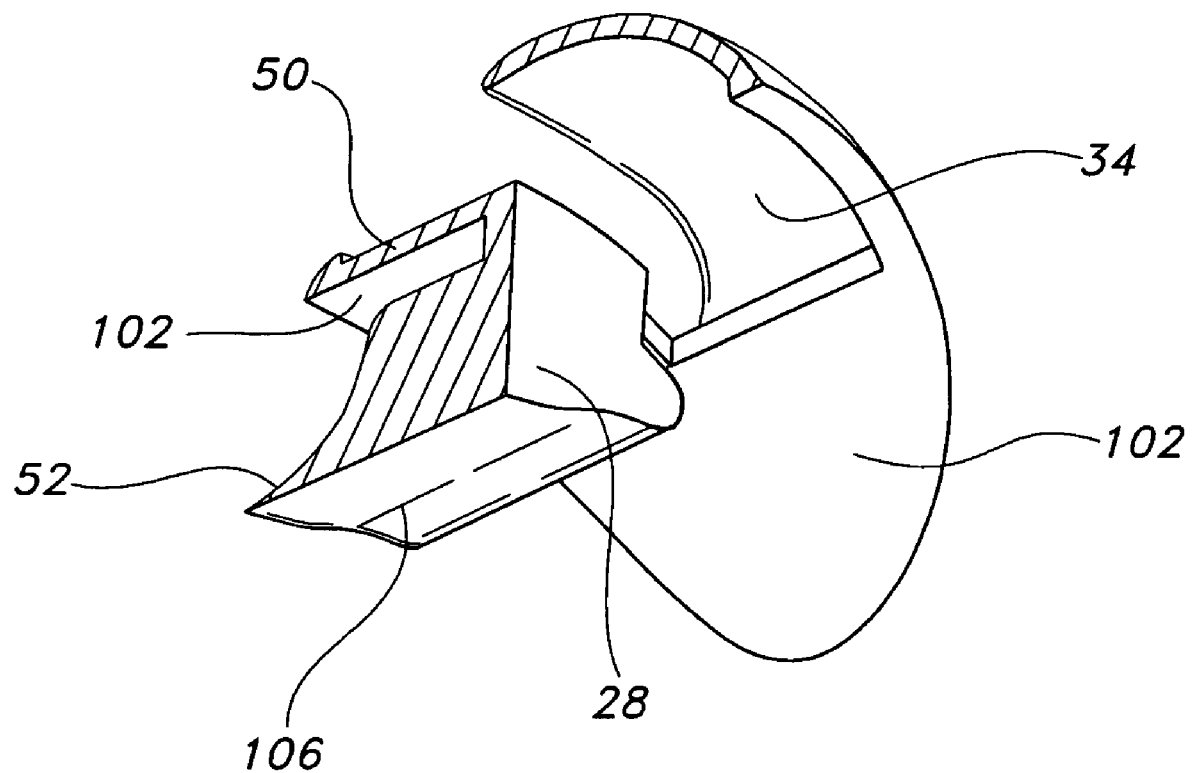
FIG. 5 is a sectional view of an alternative low profile adapter for use on a catheter.

Looking now at an alternative embodiment of the adapter 24 as depicted in the cross-sectional view of FIG. 5, it may be seen that the leading edge 52 of the plug 28 as depicted in FIGS. 3 and 4 has been substituted with a piercing member 52. The piercing member 52 may be made so that it is capable of piercing the exterior wall 18 of the cannula 12 at the position 26 thereby connecting the duct 30 to the suction lumen 16 without requiring a preformed hole in the exterior wall 18 of the cannula 12. This step may be performed during the manufacturing process, that is, at the assembly of the tracheal tube 10 prior to affixing the adapter 24 to the cannula 12. In other embodiments, not shown, the inlet 32 may be oriented on the adapter 24 in any manner desired so that suction is directed in accordance with the needs of the surgical team.

Although the above embodiments have been described primarily as being incorporated onto endotracheal tubes, it may be incorporated into other tracheal devices such as tracheostomy tubes, as well as any other application wherein it is desirable to extend the reach of suctioning away from the passage within the tube itself. As used herein and in the claims, the term "comprising" is inclusive or open-ended and does not exclude additional unrecited elements, compositional components, or method steps.

While various patents have been incorporated herein by reference, to the extent there is any inconsistency between incorporated material and that of the written specification, the written specification shall control. In addition, while the invention has been described in detail with respect to specific embodiments thereof, it will be apparent to those skilled in the art that various alterations, modifications and other changes may be made to the invention without departing from the spirit and scope of the present invention. It is therefore intended that the claims cover all such modifications, alterations and other changes encompassed by the appended claims.

We claim:

1. A tracheal tube with a suction lumen comprising:
   a cannula having a length defined by a proximal end and a distal end, the cannula having a respiratory lumen internal to the cannula extending along the length and at least one suction lumen internal to the cannula extending along the length and disposed adjacent to an exterior wall of the cannula;
   an inflatable cuff having a shape to block a trachea beneath a glottis of a patient:
   a suction source connected to the proximal end; and
   an adapter for inserting partially into the exterior wall of the cannula at a position along the length so as to be in communication with the suction lumen proximal to the inflatable cuff, the adapter comprising a plug and a duct with an inlet and an outlet, the outlet interconnecting the duct with the suction source through the suction lumen, the inlet extending the reach of the suction lumen through the duct, the plug adapted to seal the suction lumen between the adapter and the distal end.

2. The tracheal tube of claim 1 wherein the adapter is permanently affixed to the exterior wall of the cannula.

3. The tracheal tube of claim 1 wherein the adapter comprises a partial annulus.

4. The tracheal tube of claim 1 comprising a plurality of inlets for accessing the duct.

5. The tracheal tube of claim 1 wherein the adapter comprises a flexible material.

6. The tracheal tube of claim 1 wherein the adapter comprises a rigid material.

7. The tracheal tube of claim 1 wherein the adapter comprises a first wall for seating against the exterior wall of the cannula, and a second wall disposed a spaced distance from the first wall, the spaced distance comprising the duct.

8. The tracheal tube of claim 1 comprising an inflatable cuff having a shape to block a trachea beneath a glottis of the patient, the inlet oriented such that suction occurs proximal to the inflatable cuff.

9. The tracheal tube of claim 1 comprising a plurality of barbs to engage walls internal to the cannula.

10. A tracheal tube with a suction lumen comprising:
    a cannula having a length defined by a proximal end and a distal end, the cannula having a respiratory lumen extending along the length and at least one suction lumen extending along the length and disposed adjacent to an exterior wall of the cannula;
    a suction source connected to the proximal end; and
    an adapter for inserting partially into the exterior wall of the cannula at a position along the length proximal to the inflatable cuff, the adapter comprising a plug and a duct with an inlet and an outlet, the outlet interconnecting the duct with the suction source through the suction lumen, the inlet extending the reach of the suction lumen through the duct, the plug having a plurality of barbs to engage walls internal to the cannula and being adapted to seal the auction lumen between the adapter and the distal end.

* * * * *